US009361082B2

(12) United States Patent
Irwin et al.

(10) Patent No.: US 9,361,082 B2
(45) Date of Patent: Jun. 7, 2016

(54) CENTRAL MONITORING STATION WARM SPARE

(75) Inventors: John Howard Irwin, Marcellus, NY (US); Eric G. Petersen, Beaverton, OR (US); Robert Paul Wilmington, Vancouver, WA (US)

(73) Assignee: WELCH ALLYN, INC., Skaneateles Falls, NY (US)

( * ) Notice: Subject to any disclaimer, the term of this patent is extended or adjusted under 35 U.S.C. 154(b) by 530 days.

(21) Appl. No.: 13/605,348

(22) Filed: Sep. 6, 2012

(65) Prior Publication Data

US 2014/0068237 A1    Mar. 6, 2014

(51) Int. Cl.
  G06F 9/445    (2006.01)
  G06F 9/44     (2006.01)
  G06F 19/00    (2011.01)

(52) U.S. Cl.
  CPC ............... *G06F 8/61* (2013.01); *G06F 19/327* (2013.01); *G06F 19/3418* (2013.01)

(58) Field of Classification Search
  CPC ..... G06F 8/61; G06F 19/327; G06F 19/3418; G06F 8/71; G06F 8/20; G06F 9/44505
  USPC ................................................. 717/121, 176
  See application file for complete search history.

(56) References Cited

U.S. PATENT DOCUMENTS

| 5,608,865 | A    | 3/1997  | Midgely et al.       |
|-----------|------|---------|----------------------|
| 5,627,962 | A    | 5/1997  | Goodrum et al.       |
| 5,941,994 | A    | 8/1999  | DeKoning et al.      |
| 5,956,719 | A    | 9/1999  | Kudo et al.          |
| 6,616,606 | B1 * | 9/2003  | Petersen et al. ............... 600/300 |
| 6,650,932 | B1   | 11/2003 | Cohen et al.         |
| 6,744,450 | B1   | 6/2004  | Zimniewicz et al.    |
| 7,016,751 | B2   | 3/2006  | Nordquist et al.     |
| 7,082,440 | B2   | 7/2006  | Ogino et al.         |
| 7,634,507 | B2   | 12/2009 | Atluri et al.        |
| 7,716,066 | B2   | 5/2010  | Rosow et al.         |
| 8,069,227 | B2   | 11/2011 | Atluri et al.        |

(Continued)

FOREIGN PATENT DOCUMENTS

| GB | 2473303 A | 3/2011 |
| JP | 9231185 A | 9/1997 |
| WO | 0116701 A2 | 3/2001 |

OTHER PUBLICATIONS

International Search Report & Written Opinion in PCT/US2013/055056 mailed Nov. 26, 2013, 9 pages.

(Continued)

*Primary Examiner* — Anna Deng
(74) *Attorney, Agent, or Firm* — Merchant & Gould P.C.

(57) ABSTRACT

A method for preparing a computer for use as a central monitoring station includes connecting a computer to a network. An operating system is installed on the computer. Anti-virus software is installed on the computer. Licensing information is installed on the computer. Configuration information is stored on the computer. The configuration information is for the computer and at least one additional computer. A determination is made that the computer is to be activated as a first central monitoring station on the network. When the determination is made that the computer is to be activated as the first central monitoring station, the computer is configured according to a first subset of the configuration information. The computer is activated on the network as the first central monitoring station.

16 Claims, 4 Drawing Sheets

(56) References Cited

U.S. PATENT DOCUMENTS

| | | | |
|---|---|---|---|
| 2003/0014160 A1 | 1/2003 | Nordquist et al. | |
| 2006/0155912 A1* | 7/2006 | Singh et al. | 711/6 |
| 2007/0204145 A1 | 8/2007 | Bunn et al. | |
| 2008/0301489 A1 | 12/2008 | Li et al. | |
| 2008/0301777 A1 | 12/2008 | Ichikawa et al. | |
| 2009/0083443 A1* | 3/2009 | Ocko et al. | 709/248 |
| 2010/0088281 A1* | 4/2010 | Driesen et al. | 707/641 |
| 2011/0084839 A1 | 4/2011 | Groth et al. | |
| 2012/0075060 A1* | 3/2012 | Connor | 340/5.54 |
| 2012/0272094 A1* | 10/2012 | Bower et al. | 714/4.11 |

OTHER PUBLICATIONS

Meshkat, L. et al., Analysis of safety systems with on-demand and dynamic failure modes, Reliability and Maintainability Symposium, 2000, pp. 14-21.

* cited by examiner

CENTRAL MONITORING STATION WARM SPARE

BACKGROUND

In a medical setting such as a hospital, a central monitoring station provides a central location at which vital signs and other medical information for patients may be displayed. Because of the importance of displaying the vital signs and other medical information to clinicians at the hospital, it is desirable to minimize central monitoring station downtime.

One method of minimizing central monitoring station downtime is to have a backup central monitoring station for each central monitoring station on a medical network in the hospital. If the backup central monitoring station is kept up to date with configuration information, operating system changes, anti-virus changes, etc., a primary central monitoring station can be quickly replaced with the backup central monitoring station when the primary central monitoring station malfunctions.

Having a backup central monitoring station for every central monitoring station on the medical network can be very costly. A lower cost alternative, involving creating the backup central monitoring station when the primary central monitoring station fails, can result in an unacceptable amount of downtime needed to create the backup central monitoring station.

SUMMARY

Embodiments of the disclosure are directed to systems and methods for preparing a computer for use as a central monitoring station. A computer is connected to a network. An operating system is installed on the computer. Anti-virus software is installed on the computer. Licensing information is installed on the computer. Configuration information is stored on the computer. The configuration information is for the computer and at least one additional computer. A determination is made that the computer is to be installed as a first central monitoring station on the network. When a determination is made that the computer is to be installed as the first central monitoring station, the computer is configured according to a first subset of the configuration information. The computer is activated on the network as the first central monitoring station.

In another aspect, an electronic computing device comprises a processing unit and a system memory. The system memory includes instructions that when executed by the processing unit cause the electronic computing device to connect the electronic computing device to a network, install an operating system on the electronic computing device, install anti-virus software on the electronic computing device and store configuration information on the electronic computing device. The configuration information is for the electronic computing device and at least one additional computing device. A determination is made that the electronic computing device is to be activated as a first central monitoring station on the network. When a determination is made that the electronic computing device is to be activated as the first central monitoring station, the electronic computing device is configured according to a first subset of the configuration information. The electronic computing device is activated on the network as the first central monitoring station.

In yet another aspect, a computer-readable data storage medium comprises instructions that, when executed by a processing unit of a first warm-spare computer, cause the first warm-spare computer to connect to a network, install an operating system, install application software, install anti-virus software, store licensing information and store first configuration information. The first configuration information is for the first warm-spare computer, a second warm-spare computer, a first central monitoring station, and a second central monitoring station. The instructions further cause the warm-spare computer to receive updates to the operating system, receive updates to the application software, receive updates to the anti-virus software, receive updates to the first configuration information and receive updates to the licensing information. A determination is made that the first warm-spare computer is to be activated as the first central monitoring station on the network. When a determination is made that the first warm-spare computer is to be activated as the first central monitoring station, the first warm-spare computer is configured according to a first subset of the first configuration information, licensing information is activated for the first warm-spare computer from the stored licensing information and the first warm-spare computer is activated on the network as the first central monitoring station. A determination is made that the second server computer is to be configured as a second central monitoring station. When a determination is made that the second warm-spare computer is to be configured as the second central monitoring station, the second warm-spare computer is configured according to a second subset of the first configuration information, licensing information is activated for the second warm-spare computer from the stored licensing information and the second warm-spare computer is activated as the second central monitoring station. The first subset of the first configuration information and the second subset of the first configuration information are different.

The details of one or more techniques are set forth in the accompanying drawings and the description below. Other features, objects, and advantages of these techniques will be apparent from the description, drawings, and claims.

DETAILED DESCRIPTION

The present disclosure is directed to systems and methods for creating one or more warm-spare computers for a medical network. Using the systems and methods, a warm-spare computer may be quickly converted to a central monitoring station.

A central monitoring station is a computer that displays patient information at a central location, for example a nurse's station, in a medical setting. The patient information may include vital signs for the patient and administrative information for the patient such as the patient's name, location and attending physician.

A warm-spare computer is a computer, for example a PC workstation, that is installed on a network and kept up to date with operating system updates, application software updates, anti-virus updates and configuration updates, but which is not activated as a central monitoring station. However, because the warm-spare computer is kept up to date, the warm-spare computer can be quickly converted to a central monitoring station when an active central monitoring station needs to be replaced. In addition, because one warm-spare computer may be able to replace a plurality of central monitoring stations, each central monitoring station does not need a dedicated warm-spare computer. Typically, the warm-spare computers and the central monitoring station are on a medical network. However, in examples, the warm-spare computers may be on a network other than the medical network.

Figure 1:
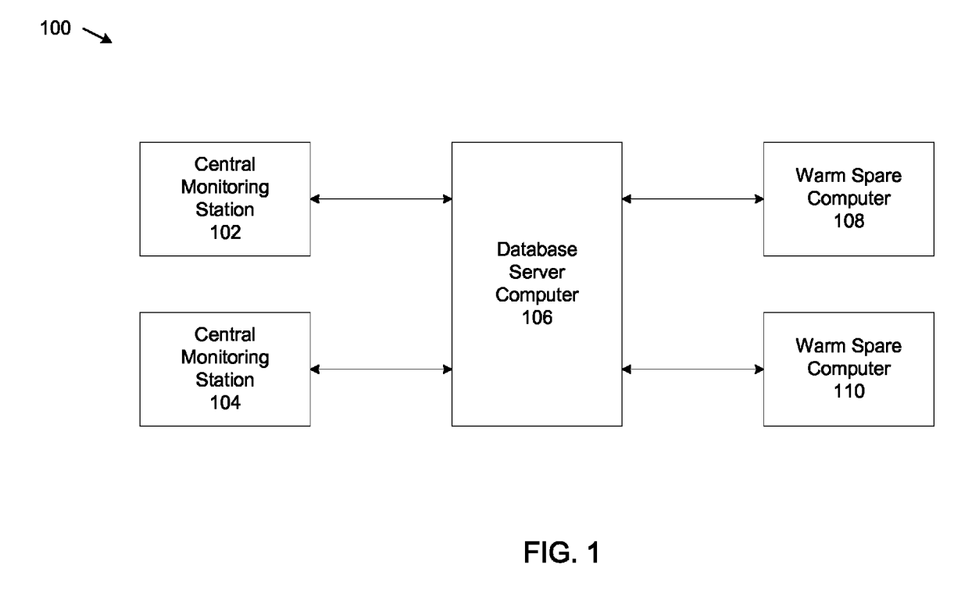
FIG. 1 shows an example system that supports warm-spare computers.

FIG. 1 shows an example system 100 which supports warm-spare computers. The example system 100 includes central monitoring station 102, central monitoring station 104, database server computer 106, warm-spare computer 108 and warm-spare computer 110.

The example central monitoring stations 102, 104 are computers that receive physiological data for a plurality of patients and which display the physiological data and other patient information on a display screen of the central monitoring stations 102, 104. The physiological data is typically received from patient monitor devices, located in the vicinity of the central monitoring stations 102, 104 that monitor physiological data for patients. The central monitoring stations 102, 104 are typically located in central locations in a medical setting, such as a nurse's station in a hospital. The central monitoring stations 102, 104 are typically installed at different locations in a hospital, for example on different floors or in different wings of a floor. Each central monitoring station 102, 104 is configured for the medical devices, for example patient monitoring devices, at the location where the central monitoring station 102, 104 is installed. A hospital may have many central monitoring stations installed.

The example database server computer 106 stores configuration information for the central monitoring stations and the warm-spare computers in the example system 100. The database server computer 106 stores a common configuration file that is kept up to date and that is periodically replicated on central monitoring stations 102, 104 and warm-spare computers 108, 110. In examples, each central monitoring station 102, 104 and each warm-spare computer 108, 110 store the same common configuration file.

Typically, central monitoring stations are initially configured as warm-spare computers. When a determination is made to create a central monitoring station, a subset of the common configuration file, applicable to the selected central monitoring station, is activated on the warm-spare computer from which the central monitoring station is created. The database server computer 106 stores a record of which configuration file subsets correspond to which central monitoring station.

The common configuration file stores a variety of configuration information. Examples of configuration information that may be stored in the common configuration file include IP addresses for each central monitoring station on the network, a name for each central monitoring station, a location for each central monitoring station, a list of patient rooms and beds covered by each central monitoring station and user configuration information for patients covered by each central monitoring station. Other types of configuration information are possible.

The example warm-spare computers 108, 110 are computers that store the common configuration file but that are not activated as central monitoring stations. The warm-spare computers 108, 110 are located on the same network as central monitoring stations 102, 104 and database server computer 106 and receive periodic updates of the common configuration file as well as operating system updates, application software updates, anti-virus updates, licensing information updates and other updates from database server computer 106.

Because warm-spare computers 108, 110 are kept up to date with configuration, operating system, application software, anti-virus, licensing and other updates, the warm-spare computers 108, 110 can be easily and quickly converted to central monitoring stations. In addition, because a warm-spare computer can be converted to any central monitoring station, there does not need to be a one-to-one ratio between warm-spare computers and central monitoring stations. In examples, only a few warm-spare computers may be needed to support a network of central monitoring stations. In other examples, warm spare-computers may also be converted to other types of computers besides central monitoring stations. For example, warm-spare computers may be converted to server computers.

In this disclosure, converting a warm-spare computer to a central monitoring station may also be referred to as activating the warm-spare computer as the central monitoring station. In general, activating the warm-spare computer as the central monitoring station includes loading the subset of the common configuration file on the warm-spare computer and transferring a license from a previously active central monitoring station to the warm-spare computer. The warm-spare computer is then activated as the central monitoring station. In some examples, activating the warm-spare computer as the central monitoring station may simply refer to initiating operation of the warm-spare computer as the central monitoring station. This assumes that the subset of the common configuration file has been previously loaded on the warm-spare computer and that the license from the previously active central monitoring station has been transferred to the warm-spare computer.

Figure 2:
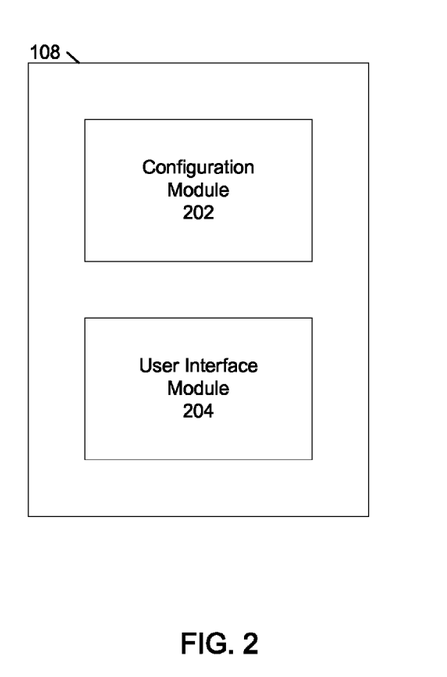
FIG. 2 shows example modules of a warm-spare computer of FIG. 1.

FIG. 2 shows example modules of warm-spare computer 108. The example warm-spare computer 108 includes a configuration module 202 and a user interface module 204. The example configuration module 202 stores the common configuration file that includes configuration information for warm-spare computers 108, 110, for central monitoring stations 102, 104 and for any additional warm-spare computers and central monitoring stations in system 100. The example user interface module 204 permits an administrator to activate a subset of the configuration information. Activating the subset of the configuration information typically converts the warm-spare computer 108 into a central monitoring station, for example central monitoring station 102 or central monitoring station 104.

The example user interface module 204 provides support for a keyboard and display screen that may be used with the warm-spare computer 108. The display screen provides a menu from which an administrator or other user can convert warm-spare computer 108 to a central monitoring station. In examples, a list of available central monitoring stations may be displayed and the administrator may select one of the available central monitoring stations. When the administrator selects one of the available central monitoring stations, warm-spare computer 108 is automatically converted to the selected central monitoring station.

In examples, when the administrator selects the central monitoring station, a portion of the common configuration file is activated on warm-spare computer 108. The portion of the common configuration file that is activated corresponds to the specific configuration and location for the selected central monitoring station. In addition, licensing information associated with the selected central monitoring station is activated on warm-spare computer 108.

In examples, the administrator may convert warm-spare computer 108 from a central location on the network, from example on a client computer (not shown in FIG. 1). When the administrator logs in to warm-spare computer 108 from the client computer, the user interface module 204 displays the menu from which the administrator may select the central monitoring station.

When the warm-spare computer 108 is activated as a central monitoring station, the user interface module 204 also provides a display screen that display patient vital signs and other patient information. In some examples, each central monitoring station may be identical and include the same size display screen. In other examples, different central monitoring stations and/or different display screens may be used.

Figure 3:
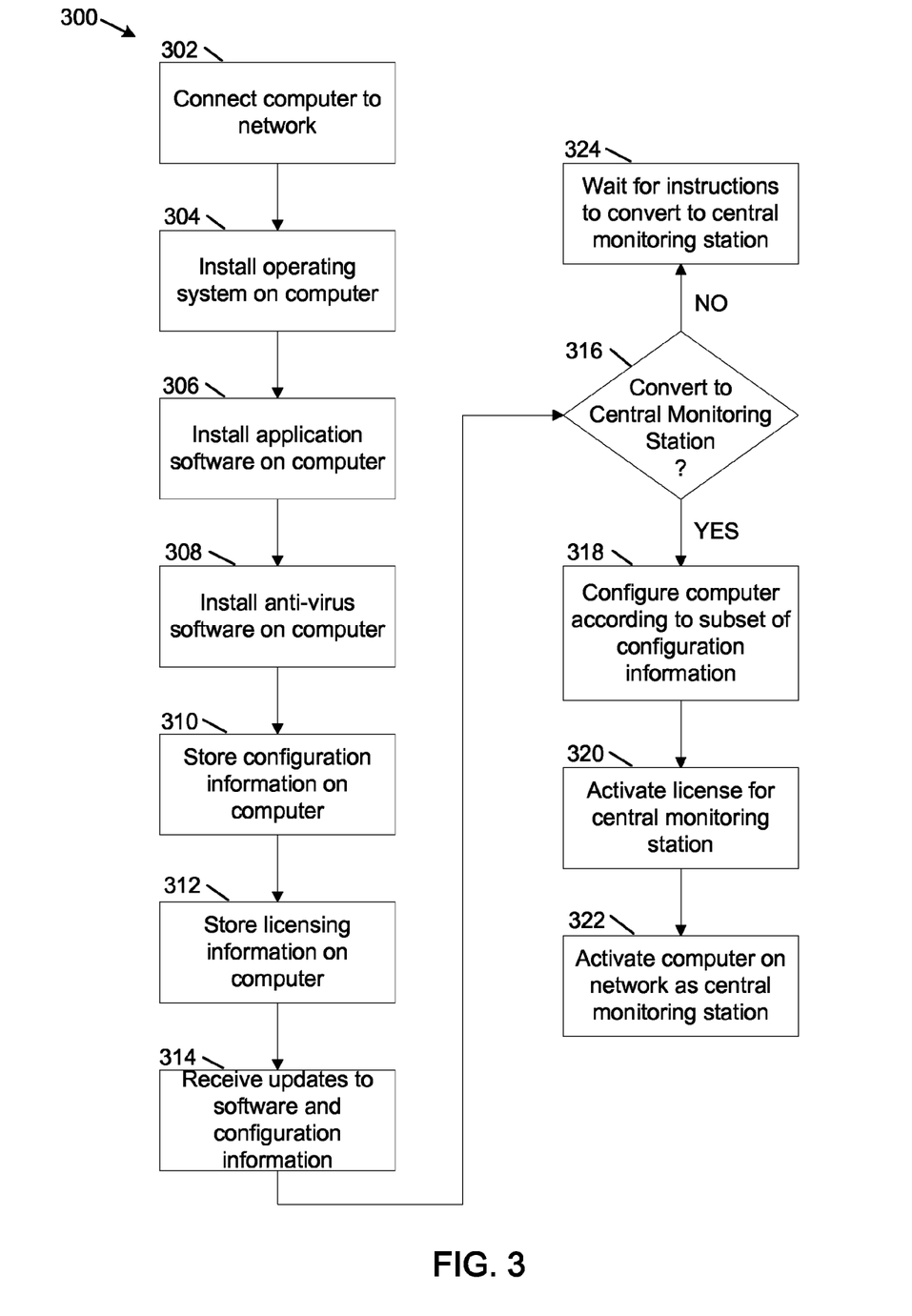
FIG. 3 shows an example flowchart of a method for converting a warm-spare computer to a central monitoring station.

FIG. 3 shows an example flowchart for a method 300 for converting a warm-spare computer to a central monitoring station. At operation 302, a computer, for example a PC workstation, is connected to a computer network. In examples, the network may be a corporate Intranet network, although other types of networks are possible. A plurality of client computers, server computers and database server computers may be connected to the network.

At operation 304, an operating system is installed on the computer. At operation 306, application software is installed on the computer. At operation 308, anti-virus software is installed on the computer.

At operation 310, configuration information is stored on the computer. In examples, the configuration information comprises settings for computers that are installed on the network. The configuration information includes whether a computer is active on the network as a central monitoring station or whether the computer is configured be a warm-spare computer. The configuration information is typically obtained from a database server computer, for example from database server computer 106. The configuration information includes configuration information for each central monitoring station on the network. In initially, a central monitoring station is configured to be a warm-spare computer.

At operation 312, licensing information is stored on the warm-spare computer. The licensing information permits the warm-spare computer to be licensed as a central monitoring station. The licensing information may include one or more software licenses. However, the one or more licenses are not activated until after a determination is made to convert the warm-spare computer to a central monitoring station.

At operation 314, updates are received for one or more of the operating system, application software, anti-virus software, configuration information and licensing information. In general, the updates are received as needed to keep the warm-spare computer up to date regarding software, and configuration and licensing information.

At operation 316, a determination is made as to whether the warm-spare computer is to be converted to a central monitoring station. Typically, a determination is made to convert a warm-spare computer to a central monitoring station when a central monitoring station on the network needs to be replaced, for example when a hardware malfunction occurs at the central monitoring station. In other examples, a warm-spare computer may be converted to a central monitoring station when the warm-spare computer is initially installed on the network or during planned preventative maintenance or replacement of a central monitoring station or server computer on the network.

In examples, when the determination is made to convert the warm-spare computer to the central monitoring station, an administrator logs on the warm-spare computer and selects the central monitoring station from a user interface. The user interface provides a menu of central monitoring stations on the network. The administrator may select a central monitoring station from the menu, typically by checking a check-box corresponding to the name of the central monitoring station. In examples, the administrator may log-on directly to the warm-spare computer or may log-on to the warm-spare computer over the network from a client computer.

At operation 316, when a determination is made to convert the warm-spare computer to the central monitoring station, at operation 318, the warm-spare computer is automatically configured to a subset of the configuration information in the configuration file stored on the warm-spare computer. The subset of the configuration information to which the warm-spare computer is configured corresponds to configuration information specific to the central monitoring station to which the warm spare is being configured.

At operation 320, the one or more licenses stored on the warm-spare computer at operation 312 are activated on the warm-spare computer. This permits the warm-spare computer to be licensed as the central monitoring station.

When the warm-spare computer is configured to the subset of the configuration information, the warm-spare computer has the configuration of the central monitoring station. At operation 322, the converted warm-spare computer is activated on the network as a central monitoring station.

At operation 316, when a determination is made not to convert the warm-spare computer to the central monitoring station, at operation 324 the warm-spare computer stays online receiving application system updates, operating system updates and configuration information updates until instructions are received to convert the warm-spare computer to a central monitoring station.

Figure 4:
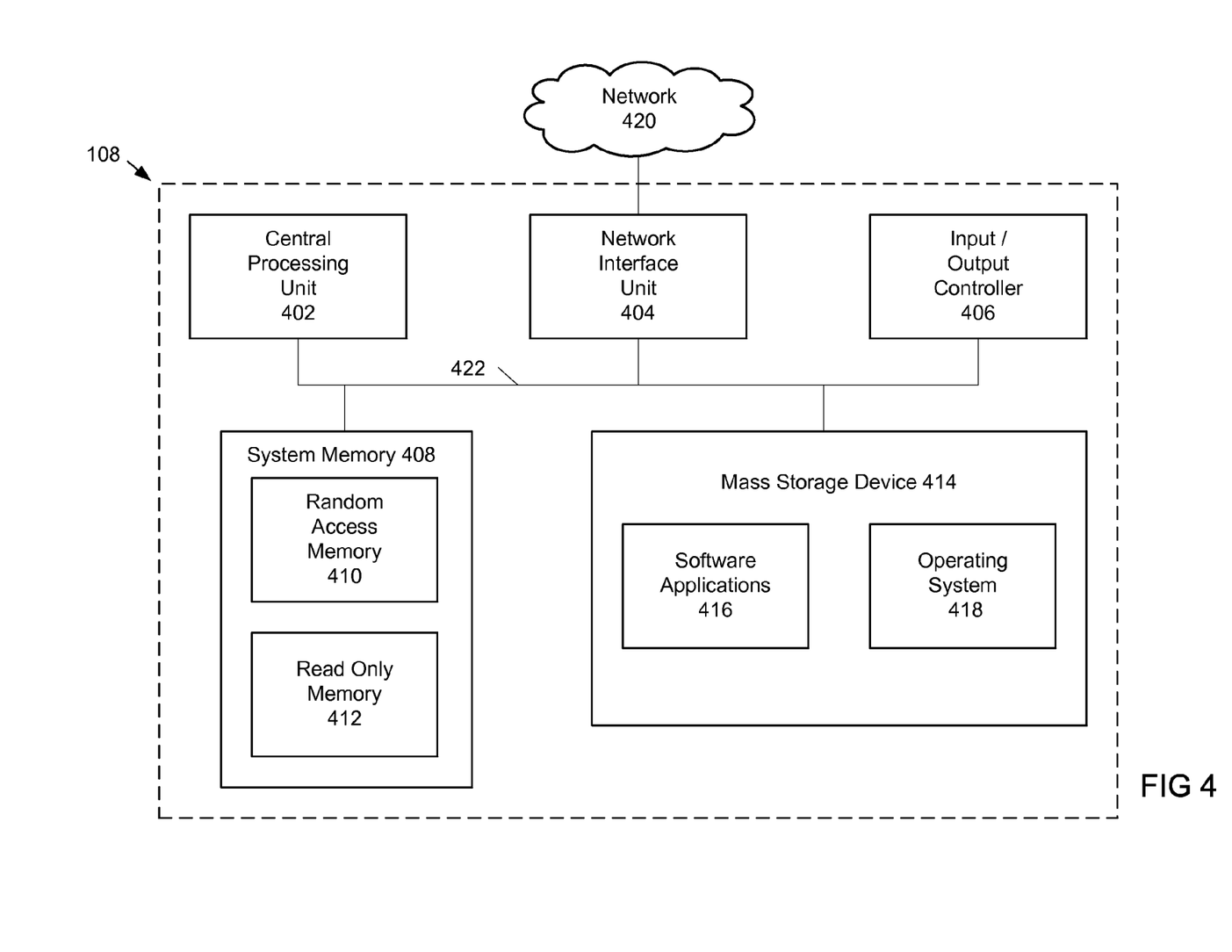
FIG. 4 shows example physical components of a warm-spare computer of FIG. 1.

FIG. 4 illustrates example physical components of the warm-spare computer 108. As illustrated in the example of FIG. 4, the warm-spare computer 108 includes at least one central processing unit ("CPU") 402, a system memory 408, and a system bus 422 that couples the system memory 408 to the CPU 402. The system memory 408 includes a random access memory ("RAM") 410 and a read-only memory ("ROM") 412. A basic input/output system contains the basic routines that help to transfer information between elements within the warm-spare computer 108, such as during startup, is stored in the ROM 412. The warm-spare computer 108 further includes a mass storage device 414. The mass storage device 414 is able to store software instructions and data.

The mass storage device 414 is connected to the CPU 402 through a mass storage controller (not shown) connected to the bus 422. The mass storage device 414 and its associated computer-readable data storage media provide non-volatile, non-transitory storage for the warm-spare computer 108. Although the description of computer-readable data storage media contained herein refers to a mass storage device, such as a hard disk or solid state disk, it should be appreciated by those skilled in the art that computer-readable data storage media can be any available non-transitory, physical device or article of manufacture from which the central display station can read data and/or instructions.

Computer-readable data storage media include volatile and non-volatile, removable and non-removable media implemented in any method or technology for storage of information such as computer-readable software instructions, data structures, program modules or other data. Example types of computer-readable data storage media include, but are not limited to, RAM, ROM, EPROM, EEPROM, flash memory or other solid state memory technology, CD-ROMs, digital versatile discs ("DVDs"), other optical storage media, magnetic cassettes, magnetic tape, magnetic disk storage or other magnetic storage devices, or any other medium which can be used to store the desired information and which can be accessed by the warm-spare computer 108.

According to various embodiments of the invention, the warm-spare computer 108 may operate in a networked environment using logical connections to remote network devices through the network 420, such as a local network, the Internet, or another type of network. The warm-spare computer 108 may connect to the network 420 through a network interface unit 404 connected to the bus 422. It should be appreciated that the network interface unit 404 may also be utilized to connect to other types of networks and remote computing systems. The warm-spare computer 108 also includes an input/output controller 406 for receiving and processing input from a number of other devices, including a keyboard, a mouse, a touch user interface display screen, or another type of input device. Similarly, the input/output controller 606 may provide output to a touch user interface display screen, a printer, or other type of output device.

As mentioned briefly above, the mass storage device 414 and the RAM 410 of the warm-spare computer 108 can store software instructions and data. The software instructions include an operating system 418 suitable for controlling the operation of the warm-spare computer 108. The mass storage device 414 and/or the RAM 410 also store software instructions, that when executed by the CPU 402, cause the warm-spare computer 108 to provide the functionality of the warm-spare computer 108 discussed in this document. For example, the mass storage device 414 and/or the RAM 410 can store software instructions that, when executed by the CPU 402, cause the warm-spare computer 108 to display received physiological data on the display screen of the warm-spare computer 108.

Although various embodiments are described herein, those of ordinary skill in the art will understand that many modifications may be made thereto within the scope of the present disclosure. Accordingly, it is not intended that the scope of the disclosure in any way be limited by the examples provided.

What is claimed is:

1. A method for preparing a first and a second computers for use as a first and a second central monitoring station among a plurality of central monitoring stations, the method comprising:
    connecting the first computer to a network of the plurality of central monitoring stations, with each of the central monitoring stations being programmed to display vital signs for a plurality of patients;
    installing an operating system on the first computer;
    installing anti-virus software on the first computer;
    installing licensing information on the first computer;
    storing first configuration information on the first computer, the first configuration information including a plurality of subsets of configuration information for the first computer and the plurality of central monitoring stations;
    determining that the first computer is to be activated as the first central monitoring station on the network;
    when a determination is made that the first computer is to be activated as the first central monitoring station, configuring the first computer according to a first subset of the first configuration information, the first subset of the first configuration information corresponding to configuration information specific to the first central monitoring station;
    determining that the second computer is to be activated as the second central monitoring station on the network;
    when a determination is made that the second computer is to be activated as the second central monitoring station, configure the second computer according to a second subset of the first configuration information, the second subset of the first configuration information being different than the first subset of the first configuration information;
    querying a central database to obtain additional configuration information for the first and second central monitoring stations, the additional configuration information including: names of the first and second central monitoring stations, locations for the first and second central monitoring stations, a list of patient rooms and beds covered by the first and second central monitoring stations, and user configuration information for patients covered by the first and second central monitoring stations; and
    activating the first computer on the network as the first central monitoring station, and the second computer on the network as the second central monitoring station.

2. The method of claim 1, wherein determining that the first computer is to be activated as the first central monitoring station comprises receiving a selection of the first central monitoring station from a menu of central monitoring stations displayed on a user interface of the first computer.

3. The method of claim 2, wherein when the selection of the first central monitoring station is received, the first computer is automatically configured to be the first central monitoring station.

4. The method of claim 1, further comprising periodically updating the first computer with operating system updates.

5. The method of claim 1, further comprising periodically updating the first computer with anti-virus software updates.

6. The method of claim 1, further comprising periodically updating the first computer with configuration information updates.

7. The method of claim 1, further comprising:
    receiving a log-on request to a user interface of the second computer;
    displaying a menu of available central monitoring stations on the user interface;
    receiving a selection of the second central monitoring station; and
    after receiving the selection of the second central monitoring station, automatically configuring the second computer to be the second central monitoring station.

8. The method of claim 1, further comprising: when a determination is made that the second computer is to be activated as the second central monitoring station, activating licensing information for the second central monitoring station.

9. The method of claim 1, wherein the the plurality of central monitoring stations includes a third computer, the third computer including the first configuration information.

10. The method of claim 9, further comprising:
    determining that the third computer is to be configured as a third central monitoring station;
    and
    when a determination is made that the third computer is to be configured as the third central monitoring station, configuring the third computer according to a third subset of the first configuration information,
    wherein the first subset of the first configuration information, the second subset of the first configuration information and the third subset of the first configuration information are different.

11. The method of claim 1, further comprising:
retrieving the first configuration information from the central database connected to the network.

12. A system comprising:
at least one processing unit, the at least one processing unit including at least one processor; and
system memory, the system memory including instructions that when executed by the at least one processing unit cause a first and a second electronic computing device to:
connect the first electronic computing device to a network of a plurality of central monitoring stations, with each of the central monitoring stations being programmed to display vital signs for a plurality of patients;
install an operating system on the first electronic computing device;
install anti-virus software on the first electronic computing device;
install licensing information on the first computing device;
store first configuration information on the first electronic computing device, the first configuration information including a plurality of subsets of configuration information for the first electronic computing device the plurality of central monitoring stations;
determine that the first electronic computing device is to be activated as a first central monitoring station on the network;
when a determination is made that the first electronic computing device is to be activated as the first central monitoring station, configure the first electronic computing device according to a first subset of the first configuration information, the first subset of the first configuration information corresponding to configuration information specific to the first central monitoring station;
determine that the second electronic computing device is to be activated as a second central monitoring station on the network;
when a determination is made that the second electronic computing device is to be activated as the second central monitoring station, configure the second electronic computing device according to a second subset of the first configuration information, the second subset of the first configuration information being different than the first subset of the first configuration information;
query a central database to obtain additional configuration information for the first and second central monitoring stations, the additional configuration information including: names of the first and second central monitoring stations, locations for the first and second central monitoring stations, a list of patient rooms and beds covered by the first and second central monitoring stations, and user configuration information for patients covered by the first and second central monitoring stations; and
activate the first electronic computing device on the network as the first central monitoring station, and the second electronic computing device on the network as the second central monitoring station.

13. The system of claim 12, wherein determine that the first electronic computing device is to be activated as the first central monitoring station comprises: receive a selection of the first central monitoring station from a menu of available central monitoring stations.

14. The system of claim 13, wherein when the selection of the first central monitoring station is received, the first electronic computing device is automatically configured to be the first central monitoring station.

15. The system of claim 12, further comprising:
determine that a third electronic computing device is to be configured as a third central monitoring station;
and
when a determination is made that the third electronic computing device is to be configured as the third central monitoring station, configure the third electronic computing device according to a third subset of the first configuration information,
wherein the first subset of the first configuration information, the second subset of the first configuration information and the third subset of the first configuration information are different.

16. The system of claim 12, further comprising:
periodically update the first electronic computing device with operating system updates;
periodically update the first electronic computing device with anti-virus software updates; and
periodically update the first electronic computing device with configuration information updates.

* * * * *